(12) United States Patent
Tanaka et al.

(10) Patent No.: US 8,939,040 B2
(45) Date of Patent: Jan. 27, 2015

(54) ANALYZING APPARATUS AND ANALYZING METHOD

(75) Inventors: Hiroyuki Tanaka, Halstenbek (DE); Hiroo Tatsutani, Kobe (JP)

(73) Assignee: Sysmex Corporation, Kobe (JP)

( * ) Notice: Subject to any disclaimer, the term of this patent is extended or adjusted under 35 U.S.C. 154(b) by 589 days.

(21) Appl. No.: 12/706,201

(22) Filed: Feb. 16, 2010

(65) Prior Publication Data

US 2010/0212438 A1    Aug. 26, 2010

(30) Foreign Application Priority Data

Feb. 20, 2009  (JP) ................................. 2009-037415

(51) Int. Cl.
*G01N 35/00*  (2006.01)
*G01N 35/02*  (2006.01)
*G01N 15/00*  (2006.01)

(52) U.S. Cl.
CPC ........ *G01N 35/026* (2013.01); *G01N 35/00603* (2013.01); *G01N 2015/0065* (2013.01)
USPC ..................................................... 73/864.81

(58) Field of Classification Search
None
See application file for complete search history.

(56) References Cited

U.S. PATENT DOCUMENTS

| 6,319,718 | B1 | 11/2001 | Matsubara et al. | ............. 436/47 |
| 6,409,968 | B1* | 6/2002 | Takahashi | ........................ 422/64 |
| 6,924,152 | B2 | 8/2005 | Matsubara et al. | ........... 436/180 |
| 2007/0231208 | A1* | 10/2007 | Tanaka et al. | ................... 422/67 |
| 2008/0310999 | A1 | 12/2008 | Yagi et al. | ........................ 422/65 |
| 2009/0292492 | A1* | 11/2009 | Nishida et al. | ................... 702/85 |

* cited by examiner

*Primary Examiner* — Robert R Raevis
(74) *Attorney, Agent, or Firm* — Brinks Gilson & Lione

(57) ABSTRACT

An analyzing apparatus comprising: a transporting device for transporting a sample; a plurality of measuring units, each measuring unit measuring a sample transported by the transporting device; a determination result obtainer for obtaining a determination result representing whether the sample requires remeasurement based on a measurement result by a predetermined measuring unit among the plurality of measuring units; a designation receiver for receiving a designation of one measuring unit for remeasuring the sample determined to be remeasured; and a transport controller for controlling the transporting device so as to transport the sample determined to be remeasured to the designated measuring unit. An analyzing method is also disclosed.

20 Claims, 12 Drawing Sheets

Fig.7

| Measuring unit configuration |
|---|

Re-examination  ⊙ YES   ◯ NO

Re-examination unit  ⊙ Same unit
　　　　　　　　　　 ◯ Other unit
　　　　　　　　　　 ◯ Assigned
　　　　　　　　　　 ◯ Unassigned    [ ▷ ]

ANALYZING APPARATUS AND ANALYZING METHOD

RELATED APPLICATIONS

This application claims priority under 35 U.S.C. §119 to Japanese Patent Application No. JP2009-037415 filed on Feb. 20, 2009, the entire content of which is hereby incorporated by reference.

FIELD OF THE INVENTION

The present invention relates to an analyzing apparatus and analyzing method for performing re-examination of a sample, provided with a plurality of measuring units, and a transport device for transporting a sample for measurement to the plurality of measuring units.

BACKGROUND OF THE INVENTION

There are known conventional analyzers capable of assaying and reassaying a sample by transporting a sample (such as whole blood, serum, plasma, urine and the like) to the measuring units, such as biochemical analyzers, immunoanalyzers, blood cell analyzers, urine analyzers and the like. In such analyzers, the analysis result of a first assay of a sample (hereinafter referred to as a first examination) is compared to a normal value to determine whether the analysis result is abnormal, and remeasurement of the sample is performed when the analysis result is determined to be abnormal.

A re-examination of a sample is necessary when the analysis result of a predetermined measurement item is outside the normal range, or when an analysis result can not be accurately obtained due to an apparatus malfunction, sample deterioration or the like. However, when the sample analysis result is outside the normal range, it is not possible to determine from the analysis result whether the cause is an apparatus malfunction or some other reason. It is therefore desirable to re-measure the sample using a different measuring unit than the measuring unit that performed the first examination.

On the other hand, there are some cases which must have priority for rapidly obtaining the results of a remeasurement. To obtain the result by re-examination at an early stage, it is desirable to transport the sample to the measuring unit nearest the sample at the moment the first examination analysis result has been obtained. Since the sample analysis result can be obtained within a few minutes after the sample has been aspirated, there is an excellent possibility that the measuring unit that performed the first examination is the measuring unit nearest the sample. Therefore, whether the re-examination of the sample should be performed by the measuring unit that performed the first examination or performed by another measuring unit must be flexibly determined according to the situation.

US Patent Publication No. 2008/0310999 discloses an automatic analysis system provided with a plurality of analysis modules, and a transport device for transporting a sample to the plurality of analysis modules. In the automatic analysis system disclosed in US Patent Publication No. 2008/0310999, the analysis module that performs the reanalysis of a sample can be specified from among three types: "completely different module," "different module priority," and "processing power priority."

When "completely different module" is specified, remeasurement is performed by a different analysis module than the analysis module that performed the first examination. When "different module" is specified, a different analysis module is a priority, however, the analysis module that performed the initial measurement may also perform the remeasurement when other analysis modules are under high load due to ongoing analyses. When "processing power priority" is specified, remeasurement is performed by the analysis module that has the greatest processing power.

SUMMARY OF THE INVENTION

The scope of the present invention is defined solely by the appended claims, and is not affected to any degree by the statements within this summary.

A first aspect of the present invention is an analyzing apparatus comprising: a transporting device for transporting a sample; a plurality of measuring units, each measuring unit measuring a sample transported by the transporting device; a determination result obtainer for obtaining a determination result representing whether the sample requires remeasurement based on a measurement result by a predetermined measuring unit among the plurality of measuring units; a designation receiver for receiving a designation of one measuring unit for remeasuring the sample determined to be remeasured; and a transport controller for controlling the transporting device so as to transport the sample determined to be remeasured to the designated measuring unit.

A second aspect of the present invention is an analyzing apparatus comprising: a transporting device for transporting a sample; a plurality of measuring units, each measuring unit measuring a sample transported by the transporting device; a determination result obtainer for obtaining a determination result representing whether the sample requires remeasurement based on a measurement result by a predetermined measuring unit among the plurality of measuring units; a time obtainer for obtaining, for each of the plurality of the measuring units, the time required to re-measure the sample determined to be remeasured; a selector for selecting, from among the plurality of measuring units, the measuring unit with the shortest time required to re-measure the sample as the measuring unit for remeasuring the sample; and a transport controller for controlling the transporting device so as to transport the sample determined to be remeasured to the selected measuring unit.

A third aspect of the present invention is an analyzing method executable by an analyzer comprising a transporting device for transporting a sample, and a plurality of measuring units, each measuring unit measuring a sample transported by the transporting device, the analyzing method comprising steps of: obtaining a determination result representing whether the sample requires remeasurement based on a measurement result by a predetermined measuring unit among the plurality of measuring units; receiving the designation of one measuring unit for remeasuring the sample determined to be remeasured; and controlling the transporting device so as to transport the sample determined to be remeasured to the designated measuring unit.

A fourth aspect of the present invention is an analyzing method executable by an analyzer comprising a transporting device for transporting a sample, and a plurality of measuring units, each measuring unit measuring a sample transported by the transporting device, the analyzing method comprising steps of: obtaining a determination result representing whether the sample requires remeasurement based on a measurement result by a predetermined measuring unit among the plurality of measuring units; obtaining, for each of the plurality of the measuring units, the time required to re-measure the sample determined to be remeasured; selecting, from among the plurality of measuring units, the measuring unit with the shortest time required to re-measure the sample as the measuring unit for remeasuring the sample; and controlling the transporting device so as to transport the sample determined to be remeasured to the selected measuring unit.

BRIEF DESCRIPTION OF THE DRAWINGS

FIG. 7 shows an example of a measuring unit configuration screen for configuring the measuring unit for performing the re-examination of a sample of the first embodiment of the analyzer of the present invention;

DETAILED DESCRIPTION OF THE PREFERRED EMBODIMENTS

First Embodiment

Figure 1:
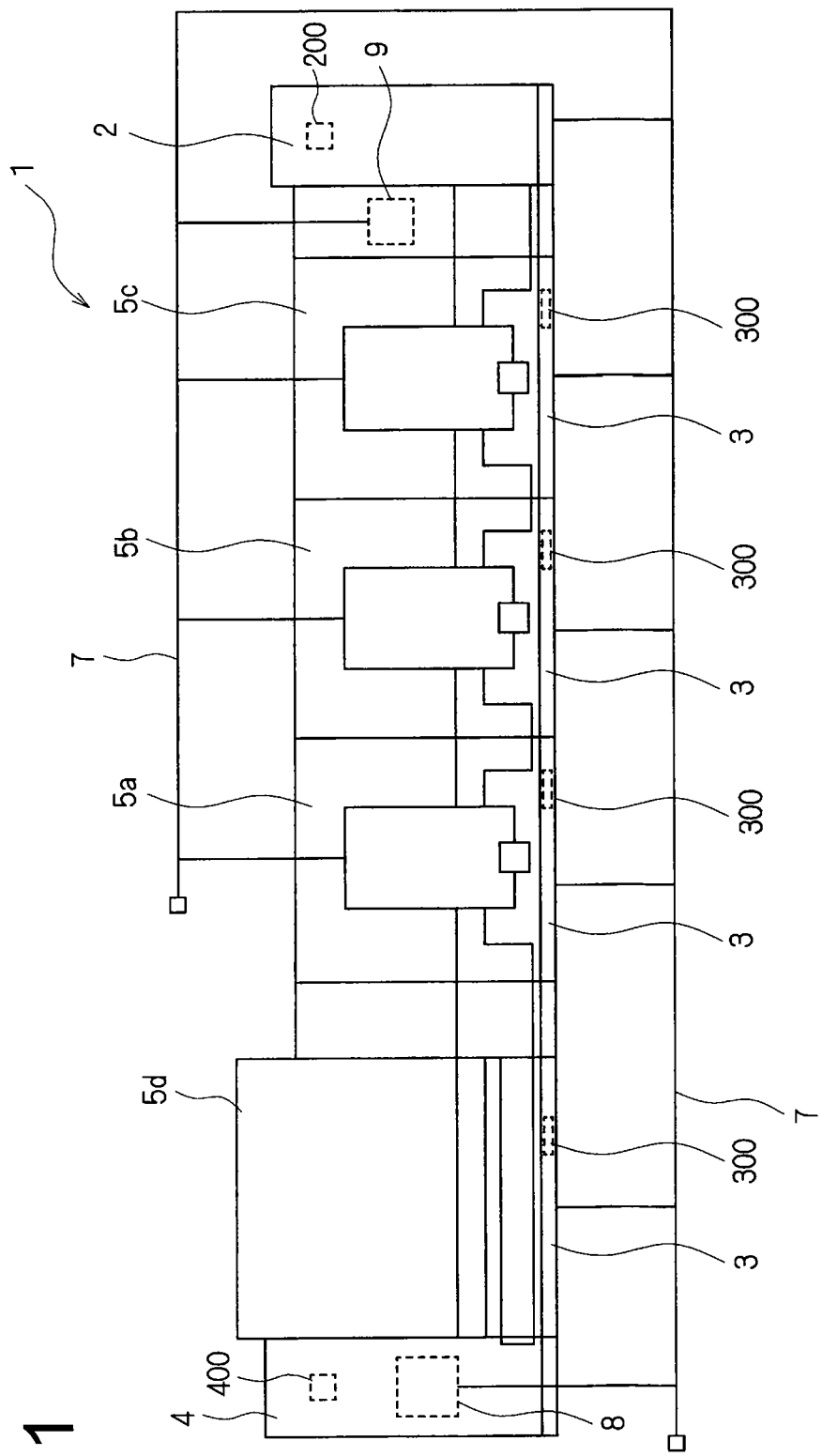
FIG. 1 is a schematic view briefly showing the structure of a first embodiment of the analyzer of the present invention.

FIG. 1 is a schematic view briefly showing the structure of a first embodiment of the analyzer of the present invention. The first embodiment of the analyzer of the present invention is provided with a sample receiver 2 for receiving a sample rack containing sample containers, measuring units 5a, 5b, 5c, 5d for measuring a sample, sample transporting devices 3 for transporting the sample rack, sample holder 4 for holding the sample rack after sample collection, and transport control device 8. The sample transporting devices 3 are respectively provided for the measuring units 5a, 5b, 5c, and 5d.

The measuring units 5a, 5b, 5c, 5d may be the same type of measuring unit, or may be different types of measuring units. The measuring units 5a, 5b, 5c, 5d are connected to a controller 9 via a LAN 7. In the first embodiment, the controller 9 controls the operations of the measuring units 5a, 5b, 5c, and 5d.

The sample receiver 2 is configured to ship a sample rack holding a plurality of sample containers to the sample transporting device 3 on the farthest right in FIG. 1. The sample receiver 2 is controlled by the transport control device 8, which is connected to the sample receiver 2 through the LAN 7 so as to be capable of data communication.

The transport control device 8 controls the sample receiver 2, sample transporting device 3, and sample holder 4 by obtaining information relating to the measuring units 5a, 5b, 5c, and 5d stored in the controller 9, for example, by obtaining identification information and information relating to the type of measuring unit.

Figure 2:
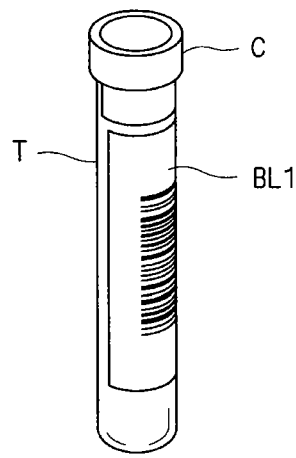
FIG. 2 is a perspective view of the exterior of a sample container.

FIG. 2 is a perspective view of the exterior of a sample container. As shown in FIG. 2, the sample container T is tube shaped with an open top end. A sample, for example blood collected from a patient, is accommodated in the interior of the sample container T, and the opening at the top end can be sealed by a cap C. A barcode label BL1 bearing a printed barcode that identifies the sample is adhered to the side surface of the sample container T.

Figure 3:
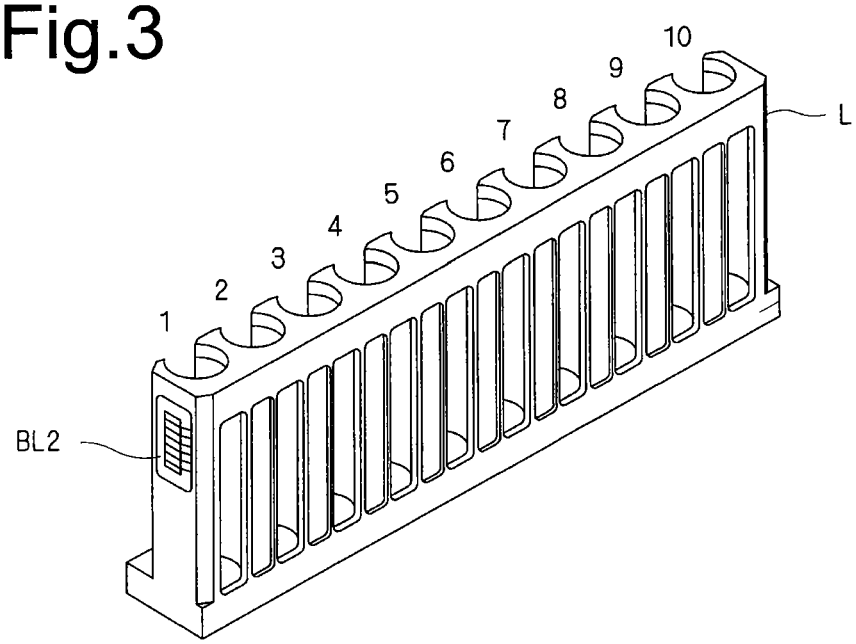
FIG. 3 is a perspective view of the exterior of a sample rack.

FIG. 3 is a perspective view of the exterior of a sample rack. As shown in FIG. 3, the sample rack L is configured so as to hold ten sample containers T in a vertical (upright) state. A barcode label BL2 bearing a printed barcode identifying the sample rack L is adhered to the side surface of the sample rack L.

In the analyzer 1 shown in FIG. 1, four sample transporting devices 3 are disposed on the front side (the side at the bottom of FIG. 1) of the measuring units 5a, 5b, 5c, and 5d. The sample rack L is delivered between adjacent sample transporting devices 3. The sample transporting device 3 farthest to the right side in FIG. 1 starts transporting the sample rack L received from the sample receiver 2. The sample transporting device 3 farthest to the left side in FIG. 1 transports the sample rack L to the sample holder 4.

Figure 4:
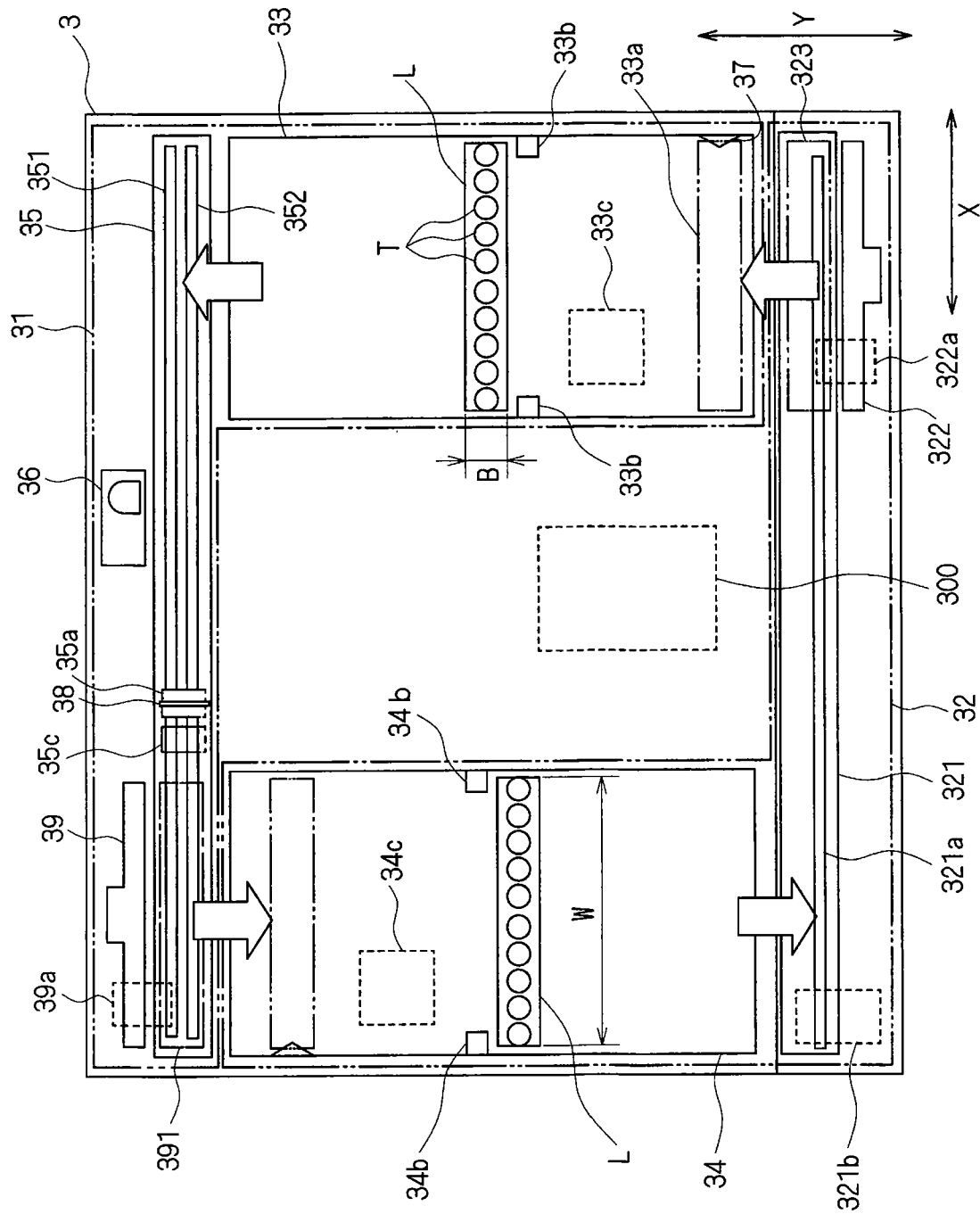
FIG. 4 is a schematic view briefly showing the structure of the sample transporting device of the first embodiment of the analyzer of the present invention.

FIG. 4 is a schematic view briefly showing the structure of the sample transporting device 3 of the first embodiment of the present invention. As shown in FIG. 4, the sample transporting device 3 is provided with a first transport mechanism 31 for supplying a sample to a measuring unit, a second transport mechanism 32 for transporting a sample to a sample transporting device 3 (or sample holder 4) on the downstream side, and a controller 300 for controlling the second transport mechanism 32. The first transport mechanism 31 is provided with a pre-analysis rack holder 33 capable of temporarily holding a plurality of sample racks L accommodating sample containers T that contain samples to be analyzed, a rack transporter 35 for linearly moving horizontally the sample rack L in the X direction in the drawing, a barcode reader 36 for reading the barcode label adhered to the sample rack L, a rack sensor 37 for detecting the presence of the sample rack L, sample container sensor 38 for detecting the presence of the sample container T, and a rack mover 39 for delivering the sample rack L to a post-analysis rack holder 34.

The reanalysis rack holder 33 is quadrilateral in shape in planar view, with a width slightly larger than the width of the sample rack L. The reanalysis rack holder 33 becomes lower in stages from the circumferential surface so that the unanalyzed sample rack L is mounted on the top surface. The sample rack L is delivered from the second transport mechanism 32 to the reanalysis rack holder 33 by the rack feeder 322 of the second transport mechanism 32, which is described later.

The rack sensor 37 is mounted near the reanalysis rack holder 33, and the position at which the sample rack L is detected by the rack sensor 37 is the rack detection position 33a. The sample rack L is transported from the second transport mechanism 32 to the rack detection position 33a, where the rack sensor 37 detects the transported sample rack L.

A rack feeder 33b, which is capable of extending toward the inner side, is provided on both side surfaces of the reanalysis rack holder 33. When the sample rack L has been detected by the rack sensor 37, the sample rack L is moved backward when the sample rack L engages the extended rack feeder 33b and is moved in this engaged state in a backward direction (a direction approaching the rack transporter 35). The rack feeder 33b is driven by a stepping motor 33c provided below the reanalysis rack holder 33.

The rack transporter 35 transports, in the X direction, the sample rack L delivered by the reanalysis rack holder 33. The sample container detection position 35a at which the sample container T is detected by the sample container sensor 38, and the sample supplying position 35c at which the sample is supplied to the measuring unit are present on the transport path of the sample rack L moved by the rack transporter 35. The rack transporter 35 moves the sample rack L through the sample container detection position 35a to the sample supplying position 35c.

The sample supplying position 35c is a position downstream the distance of one sample in the transport direction from the sample container detection position 35a, so that when a sample is transported to the sample supplying position 35c by the rack transporter 35, the sample container T is grasped by the hand of the measuring unit and removed from the sample rack L, and the sample is supplied to the measuring unit by aspirating the sample from the sample container T. After the rack transporter 35 has transported the sample container T to the sample supplying position 35c, the transport of the sample rack L is stopped while the supplying of the sample is completed and the sample container T is returned to the sample rack L.

The rack transport 35 has two belts, a first belt 351 and a second belt 352, which operate independently. The widths in the arrow Y direction of the first belt 351 and second belt 352 are respectively less than half of the width B of the sample rack L in the arrow Y direction. The first belt 351 and second belt 352 are arranged in parallel so as to not protrude beyond the width B in the arrow Y direction of the sample rack L when the sample rack L is transported by the rack transporter 35. The sample rack L can be transported in the X direction and the opposite direction by controlling the movement direction of the first belt 351 and second belt 352.

The barcode reader 36 reads the barcode of the barcode label BL1 adhered to the sample container T, and reads the barcode of the barcode label BL2 adhered to the sample rack L as shown in FIGS. 2 and 3. The barcode reader 36 reads the sample barcode of the sample container T as the sample container T is rotated in a horizontal direction by a rotating device while held in the sample rack L. Even when the barcode label BL1 of the sample container T is positioned on the opposite side from the barcode reader 36, the barcode label BL1 can be turned toward the barcode reader 36 by rotating the sample container T, thus allowing the barcode reader 36 to read the sample barcode. The rack barcode of the sample rack L records the rack ID allocated to each sample rack L, and this information is used in managing the sample analysis results.

The rack sensor 37 and the sample container sensor 38 are contact type sensors, respectively configured by a contact piece, light emitting element for emitting light, and light receiving element. The rack sensor 37 and the sample container sensor 38 are curved by the contact piece coming into contact with a detection object, and as a result the light emitted from the light emitting element is reflected by the contact piece and impinges the light receiving element. Thus, the sample container T can be detected as the contact piece is bent by the sample container T when the detection object, that is the sample container T containing the sample, passes below the sample container sensor 38.

The rack mover 39 is disposed so as to face the post-analysis rack holder 34 with the rack transporter 35 interposed therebetween, and the rack mover 39 is moved horizontally in the Y direction via the drive force of a stepping motor 39a. Thus, the sample rack L is pushed into the post-analysis rack holder 34 by moving the rack mover 39 to the post-analysis rack holder 34 side when the sample rack L is transported to a position 391 between the post-analysis rack holder 34 and the rack mover 39 (hereinafter referred to as post-analysis rack transport position). The analyzed sample rack L is therefore moved from the first transport mechanism 31 to the second transport mechanism 32.

The second transport mechanism 32 is configured by the rack mover 321, rack feeder 322, and post-analysis rack holder 34. The rack mover 321 extends in the arrow X direction in the drawing, and is capable of linearly moving horizontally the sample rack L in the arrow X direction. The rack mover 321 has an endless belt 321a and a stepping motor 321b, and the belt 321a is moved in the arrow X direction by the drive force of the stepping motor 321b. The sample rack L mounted above the belt 321a can therefore be transported in the X direction.

The rack feeder 322 is positioned on the front side of the reanalysis rack holder 33 so as to face the reanalysis rack holder 33 with the rack mover 321 interposed therebetween, and is linearly moved horizontally in the Y arrow direction by the drive force of the stepping motor 322a. Thus, the sample rack L is pushed to the rack detection position 33a within the reanalysis rack holder 33 by moving the rack feeder 322 to the reanalysis rack holder 33 side when the sample rack L is transported to a position 323 between the reanalysis rack holder 33 and the rack feeder 322 (hereinafter referred to as reanalysis rack transport position).

The post-analysis rack holder 34 is quadrilateral in shape in the planar view, with a width slightly larger than the width of the sample rack L. The post-analysis rack holder 34 becomes lower in stages from the circumferential surface so that the analyzed sample rack L is mounted on the top surface. The sample rack L is delivered from the rack transporter 35 to the post-analysis rack holder 34 by the rack mover 39.

A rack feeder 34b, which is capable of extending toward the inner side, is provided on both side surfaces of the post-analysis rack holder 34. When the sample rack L has been moved by the rack mover 39, the sample rack L is then moved forward when the sample rack L is engaged by the extended rack feeder 34b and moved forward in the engaged state (in a direction approaching the rack mover 321). The rack feeder 34b is driven by a stepping motor 34c provided below the post-analysis rack holder 34.

The sample rack L transporting operation performed by the sample transporting device 3 is controlled by the transport control device 8, which is connected to the sample transport device 3 via the LAN 7 so as to be capable of data communication. That is, the transport control device 8 controls the operation of receiving the sample rack L performed by the sample receiver 2, the operation of transporting the sample rack L performed by the sample transporting device 3, and the operation of receiving the sample rack L performed by the sample holder 4.

Note that the sample receiver 2, sample transporting device 3, and sample holder 4 are respectively provided with a controller 200, 300, 400, which is configured by a CPU, ROM, RAM and the like, as shown in FIG. 1. The transport control device 8 is capable of controlling the operations of the sample receiver 2, sample transporting device 3, and sample holder 4 via data communication with the controllers 200, 300, 400 of the sample receiver 2, sample transporting device 3, and sample holder 4. The control device 9 is also connected so as to be capable of data communication with the controllers 200, 300, 400 of the sample receiver 2, sample transporting device 3, and sample holder 4.

Figure 5:
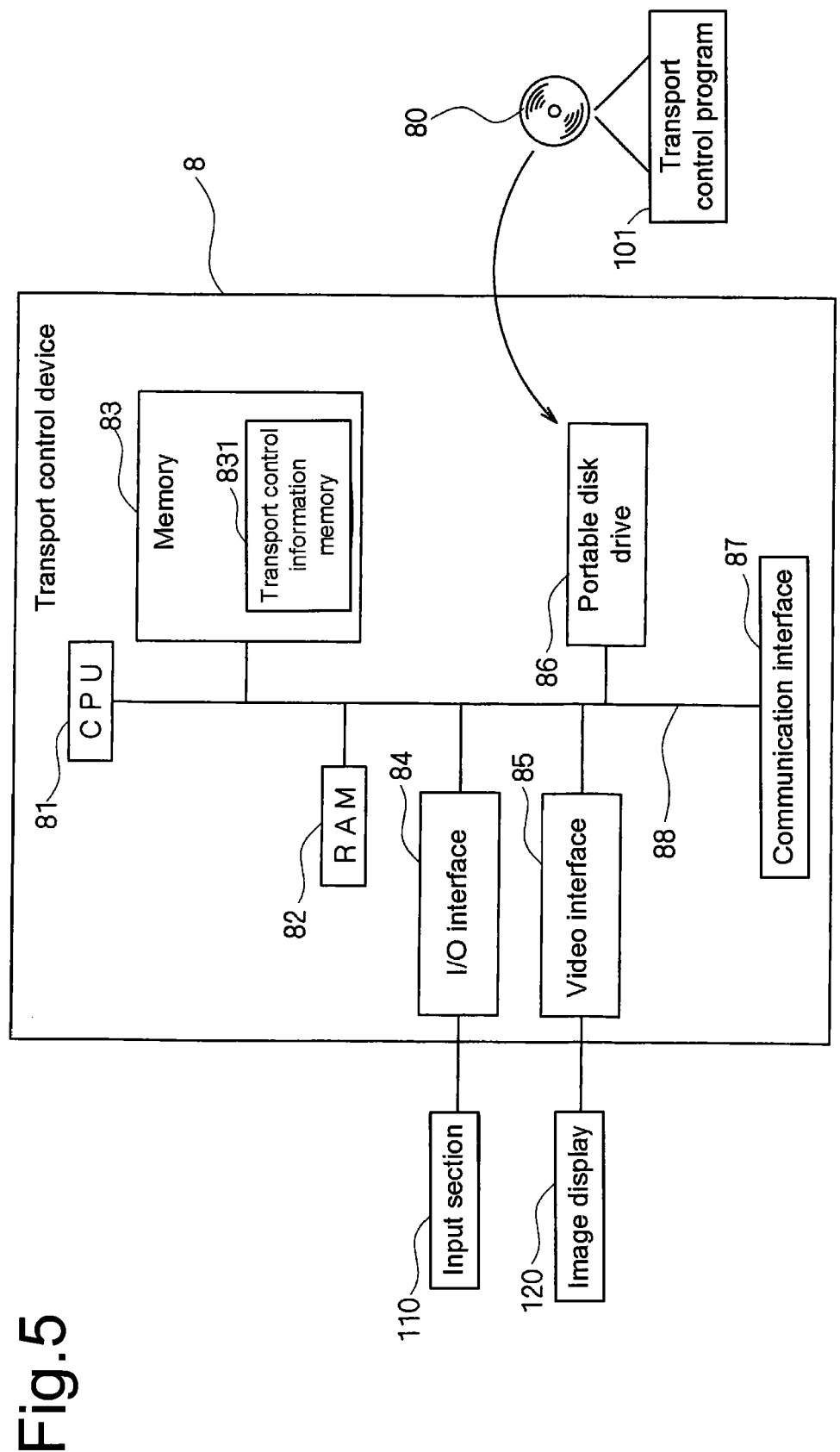
FIG. 5 is a block diagram showing the structure of the transport control device of the first embodiment of the present invention.

FIG. 5 is a block diagram showing the structure of the transport control device 8 of the first embodiment of the present invention. As shown in FIG. 5, the transport control device 8 is configured by a CPU 81, RAM 82, memory 83, I/O interface 84, video interface 85, portable disk drive 86, communication interface 87, and an internal bus 88, which is connected to all these hardware components.

The CPU 81 is connected to each hardware component of the transport control device 8 via the internal bus 88, so as to control the operation of each hardware component, and execute the functions of various software in accordance with a transport control program 101 stored in the memory 83. The RAM 82 is a volatile memory such as SRAM, DRAM or the like, and is used to expand loaded modules during the execution of the transport control program 101, and to store the temporary data generated during the execution of the transport control program 101.

The memory 83 is configured by an internal fixed storage device (hard disk), ROM or the like. The transport control program 101 stored in the memory 83 may be downloaded by the portable disk drive 86 from a portable recording medium 80 such as a DVD or CD-ROM on which information such as programs and data are recorded, and expanded from the memory 83 to the RAM 82 during execution of the program. Of course, computer programs such as the transport control program 101 may also be downloaded from a peripheral computer connected to an external network through the communication interface 87.

The memory 83 is also provided with a transport control information memory 831 for storing transport control information such as configuration item information and the like for transport control according to the type of measuring unit connected to the LAN 7.

The communication interface 87 is connected to the internal bus 88 so as to be capable of sending and receiving data to/from an external computer by means of connection to an external network such as a LAN, WAN, or the Internet. In the first embodiment, the control device 9, sample transporting devices 3 and the like are connected via the LAN 7.

The I/O interface 84 is connected to an input unit 110 such as a keyboard and mouse or the like, so as to receive data input. The video interface 85 is also connected to an image display unit 120 such as a CRT monitor, LCD or the like, so as to display predetermined images.

The measuring units 5a, 5b, 5c, 5d may be all of the same type or may be of different types. In the first embodiment, the measuring units 5a, 5b, 5c are all of the same type, but the remaining measuring unit 5d is a different type of measuring unit. Specifically, the measuring units 5a, 5b, 5c are blood cell counters for counting blood cells using both an electrical resistance method and optical method. The measuring unit 5d is a smear sample preparing device for preparing a smear sample.

Note that the measuring units 5a, 5b, 5c, 5d are not limited to these types and may be urine analyzers, blood coagulation measuring devices, immunoanalyzers, gene amplification measuring apparatuses or the like.

Figure 6:
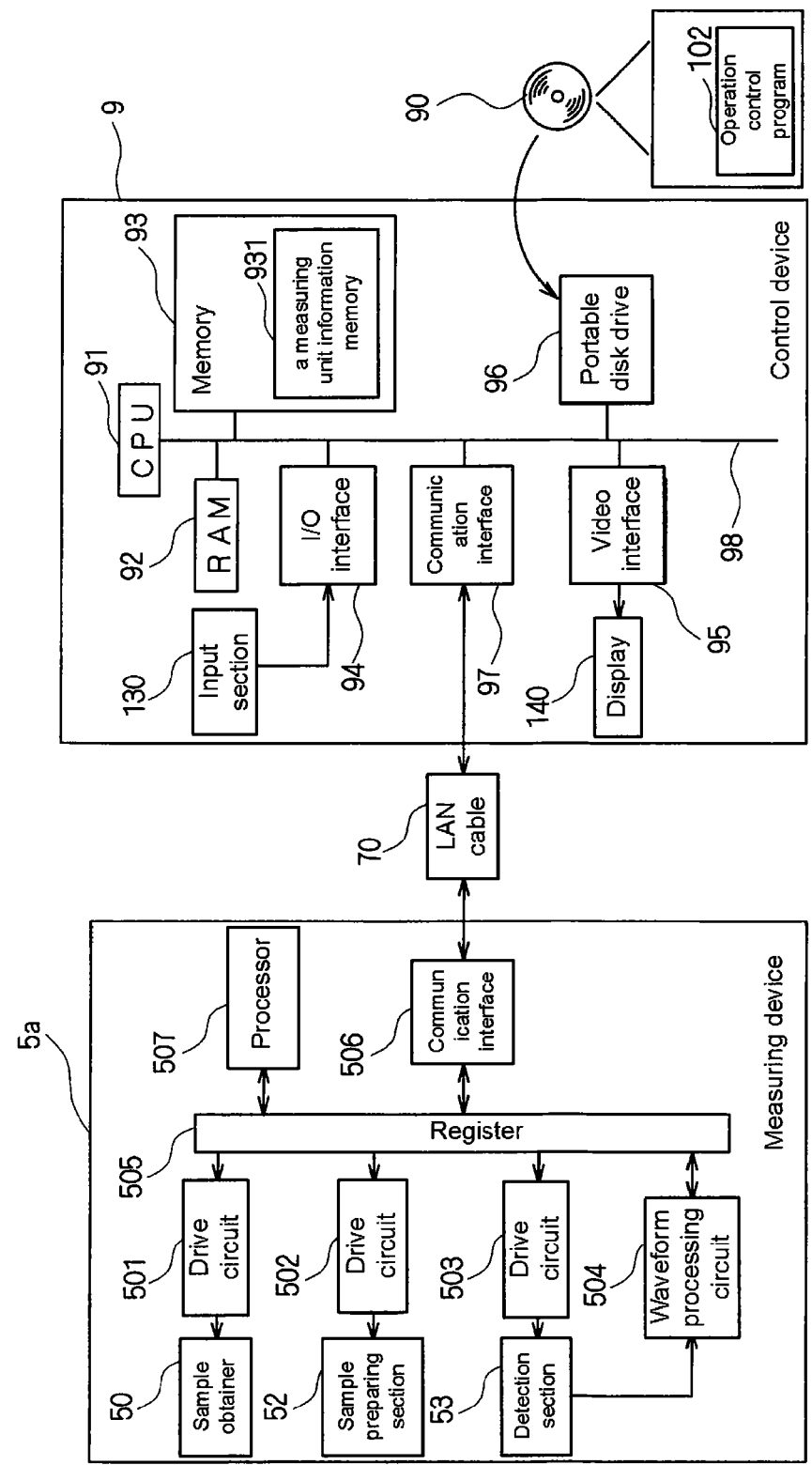
FIG. 6 is a block diagram showing the structure of the controller and the measuring unit of the first embodiment of the analyzer of the present invention.

FIG. 6 is a block diagram showing the structure of the control device 9 and measuring units 5a, 5b, 5c, 5d of the first embodiment of the present invention. In the example of FIG. 6, a structural example is shown of the blood cell counting apparatus, that is, measuring unit 5a (5b, 5c). As shown in FIG. 6, the measuring unit 5a (5b, 5c) is configured by a sample obtainer 50, drive circuit 501 for driving the sample obtainer 50, sample preparing section 52, drive circuit 502 for driving the sample preparing section 52, detection section 53, drive circuit 503 for driving the detection section 53, and waveform processing circuit 504 for performing waveform processing of the electrical signals output from the detection section 53.

The sample obtainer 50 and sample preparing section 52 are respectively driven by the drive circuit 501 and the drive circuit 502 via control signals corresponding to control data stored in a register 505. The detection section 53 converts, for example, the obtained optical signals to electrical signals. The waveform processing circuit 504 amplifies the electrical signals converted and transmitted by the detection section 53, and performs waveform processing of the amplified electrical signals. The register 505 stores the electrical signals that have been subjected to waveform processing by the waveform processing circuit 504.

The communication interface 506 is a LAN interface connected by a LAN cable 70 to a communication interface 97 of the control device 9. Thus, a processor 507 transmits information relating to the measuring unit 5a (5b, 5c) to the control device 9 when a transmission request signal for information relating to the measuring unit 5a (5b, 5c) is received from the control device 9.

The control device 9 is configured by a CPU 91, RAM, 92, memory 93, I/O interface 94, video interface 95, portable disk drive 96, communication interface 97, and an internal bus 98 connecting these hardware components.

The CPU 91 is connected to each hardware component of the control device 9 via the internal bus 98, so as to control the operation of each hardware component, and execute the functions of various software in accordance with an operation control program 102 stored in the memory 93. The RAM 92 is a volatile memory such as SRAM, DRAM or the like, and is used to expand loaded modules during the execution of the operation control program 102, and to store the temporary data generated during the execution of the operation control program 102.

The memory 93 is configured by an internal fixed storage device (hard disk), ROM or the like. The operation control program 102 stored in the memory 93 may be downloaded by the portable disk drive 96 from a portable recording medium 90 such as a DVD or CD-ROM on which information such as programs and data are recorded, and expanded from the memory 93 to the RAM 92 during execution of the program. Note that computer programs such as the operation control program 102 may also be downloaded from a peripheral computer connected to an external network through the communication interface 97.

The memory 93 is provided with a measuring unit information memory 931 for storing measuring unit information including the identification information of the connected measuring units 5a, 5b, 5c, 5d, and information relating to the measured results.

The communication interface 97 is connected to the internal bus 98 so as to be capable of sending and receiving data to/from an external computer by means of connection to an external network such as a LAN, WAN, or the Internet. In the first embodiment, the control device 9 is connected to the transport control device 8 and sample transporting devices 3 and the like via the LAN 70.

The I/O interface 94 is connected to an input unit 130 such as a keyboard and mouse or the like, so as to receive data input. The video interface 95 is also connected to an image display unit 140 such as a CRT monitor, LCD or the like, so as to display predetermined images.

In the analyzer of the first embodiment of the present invention, the measuring unit 5a performs the first examination of the sample, and a determination is made as to whether a re-examination must be performed. When it has been determined that re-examination is required, the sample to be re-examined must be transported to the measuring unit which is to perform the re-examination. That is, when the re-examination is to be performed by the measuring unit that performed the first examination, the sample rack L holding the sample container T containing the sample to be re-examined must be transported back to the sample supplying position 35c. When the re-examination is performed by the measuring unit 5b or 5c, which is a different measuring unit from the measuring unit 5a that performed the first examination, the sample rack L holding the sample container T containing the sample to be re-examined must be transported to the measuring unit 5b or 5c.

Configurations preset by the user through the image display 120 of the transport control device 8 are received beforehand whether the re-examination of the sample is performed by the measuring unit 5a or one of the measuring units 5b or 5b. FIG. 7 shows an example of a measuring unit configuration screen for configuring the measuring unit for performing the re-examination of a sample of the first embodiment of the analyzer 1 of the present invention.

In the measuring unit configuration screen shown in FIG. 7, a configuration for whether to perform a re-examination is first received by clicking a mouse or the like on a radio button or the like. This configuration may also be received through a selection button or the like on a pulldown menu. Note that an erroneous configuration can be avoided before the occurrence by validating the radio button of the re-examination unit configuration only when a "perform re-examination" configuration has been received.

When a "perform re-examination" configuration has been received, the configuration of the measuring unit to perform the re-examination (re-examination measuring unit) may then be received. When a "same unit" configuration has been received, the sample determined to require re-examination is re-examined by the measuring unit 5a that performed the first examination. Therefore, instructions are transmitted from the CPU 81 of the transport control device 8 to transport the sample rack L holding the sample container T containing the sample to be re-examined back to the sample supplying position 35c of the measuring unit 5a.

When a "different unit" configuration has been received, the sample determined to require re-examination is re-examined by either the measuring unit 5b or 5c. Note that performing the re-examination by either the measuring unit 5b or 5c can be selected based on predetermined selection conditions that have been set previously. For example, the measuring unit nearest the detected position of the sample rack L holding the sample container T containing the sample to be re-examined may be selected, or the measuring unit with the fewest number of sample racks L awaiting examination may be selected by precounting the number of sample racks L being transported to the respective measuring units 5b and 5c. The measuring unit that has the lightest processing load may also be selected by precalculating the processing loads of the processors 507 of the respective measuring units 5b and 5c. Instructions are then transmitted from the CPU 81 of the transport control device 8 to transport the sample rack L holding the sample container T containing the sample to be re-examined to the sample supplying position 35c of the selected measuring unit 5b or 5c.

When an "assign" configuration has been received, the sample determined to require re-examination is re-examined by the measuring unit assigned by the user. Assigning a measuring unit may also be accomplished by, for example, a pulldown menu. In this case, instructions are transmitted from the CPU 81 of the transport control device 8 to transport the sample rack L holding the sample container T containing the sample to be re-examined to the sample supplying position 35c of the assigned measuring unit.

When an "unassigned" configuration has been received, the sample determined to require re-examination is re-examined by a measuring unit selected based on a predetermined condition. Note that the selection of any measuring unit may be accomplished by presetting predetermined selection conditions. For example, the measuring unit nearest the sample rack L holding the sample container T containing the sample to be re-examined at the moment the transport control device 8 has received the re-examination order signal from the control device 9 may be selected, or the measuring unit with the fewest number of sample racks L awaiting examination may be selected by precounting the number of sample racks L being transported to the respective measuring units 5a, 5b, and 5c.

The measuring unit that has the lightest processing load may also be selected by precalculating the processing loads of the processors 507 of the respective measuring units 5a, 5b, and 5c. Instructions are then transmitted from the CPU 81 of the transport control device 8 to transport the sample rack L holding the sample container T containing the sample to be re-examined to the sample supplying position 35c of the selected measuring unit.

The selection information of the measuring unit for performing the re-examination, which has been configured on the measuring unit configuration screen shown in FIG. 7, is stored in the transport control information memory 831 of the transport control device 8. The CPU 81 of the transport control device 8 obtains the information relating to the transport priority of the sample to be re-examined by referencing the selection information of the measuring units stored in the transport control information memory 831.

Figure 8:
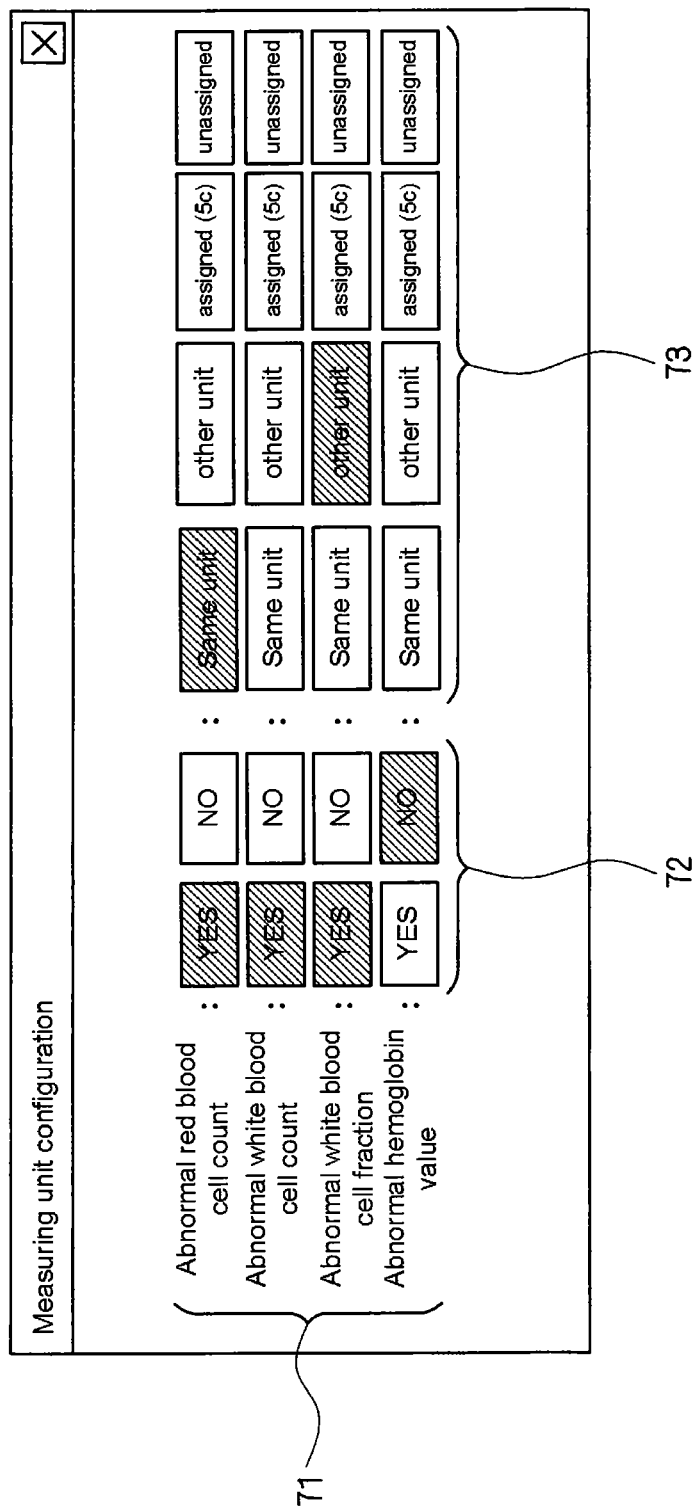
FIG. 8 shows an example of a configuration screen for configuring each measurement item of the measuring unit for performing the re-examination of a sample of the first embodiment of the analyzer of the present invention.

The configuration of the measuring unit for performing the re-examination may also be received for each measurement item. In this case, a plurality of measurement items are pre-stored as determination conditions in the memory 83 of the transport control device 8, and the configuration of the selection conditions of the measuring unit are received when re-examination is to be performed for individual measurement items. FIG. 8 shows an example of a configuration screen for configuring each measurement item of the measuring unit for performing the re-examination of the first embodiment of the analyzer 1 of the present invention.

In the measuring unit configuration screen shown in FIG. 8, the configuration of whether to perform re-examination is received for each measurement item 71 by clicking the mouse or the like on a button 72. This configuration may also be received through a radio button or the like on a pulldown menu. The items displayed in the measurement items 71 are read from the measurement items stored as determination conditions in the memory 83. In FIG. 8, the items received for the configuration are batched. Note that an erroneous configuration can be avoided before the occurrence by validating the radio button of the re-examination unit configuration only when a "perform re-examination" configuration has been received.

The "same unit" configuration is specified in the example of FIG. 8 in relation to the "abnormal red blood cell count" and "abnormal white blood cell count" configuring the measuring unit for performing the re-examination when an abnormality has been detected in the red blood cell count and white blood cell count measurement items. In this case, the sample determined to require re-examination is re-examined by the measuring unit 5a. Therefore, instructions are transmitted from the CPU 81 of the transport control device 8 to transport the sample rack L holding the sample container T containing the sample to be re-examined back to the sample supplying position 35c of the measuring unit 5a.

The "other unit" configuration is specified in the example of FIG. 8 in relation to the "white blood cell fraction" configuring the measuring unit for performing the re-examination when an abnormality has been detected in the white blood cell fraction measuring item. In this case, the sample determined to require re-examination is re-examined by the measuring unit 5b or 5c. Note that the selection of either measuring unit 5b or 5c may also be accomplished by presetting a predetermined selection condition. For example, the measuring unit nearest the detected position of the sample rack L holding the sample container T containing the sample to be re-examined may be selected, or the measuring unit with the fewest number of sample racks L awaiting examination may be selected by precounting the number of sample racks L being transported to the respective measuring units 5b and 5c. The measuring unit that has the lightest processing load may also be selected by precalculating the processing loads of the processors 507 of the respective measuring units 5b and 5c. Instructions are then transmitted from the CPU 81 of the transport control device 8 to transport the sample rack L holding the sample container T containing the sample to be re-examined to the sample supplying position 35c of the selected measuring unit 5b or 5c.

When the "assign 5c" configuration is received, the sample determined to require re-examination is re-examined by the assigned measuring unit 5c. Although only the measuring unit 5c is assigned in the example of FIG. 8, such assignment is not specifically limited. In this case, instructions are then transmitted from the CPU 81 of the transport control device 8 to transport the sample rack L holding the sample container T containing the sample to be re-examined to the sample supplying position 35c of the assigned measuring unit 5c.

When an "unassigned" configuration has been received, the sample determined to require re-examination is re-examined by a measuring unit assigned based on a predetermined condition. Note that the selection of any measuring unit may be accomplished by presetting predetermined selection conditions. For example, the measuring unit nearest the sample rack L holding the sample container T containing the sample to be re-examined at the moment the transport control device 8 has received the re-examination order signal from the control device 9 may be selected, or the measuring unit with the fewest number of sample racks L awaiting examination may be selected by precounting the number of sample racks L being transported to the respective measuring units 5a, 5b, and 5c. The measuring unit that has the lightest processing load may also be selected by precalculating the processing loads of the processors 507 of the respective measuring units 5a, 5b, and 5c. Instructions are then transmitted from the CPU 81 of the transport control device 8 to transport the sample rack L holding the sample container T containing the sample to be re-examined to the sample supplying position 35c of the selected measuring unit.

The selection information of the measuring unit for performing the re-examination, which has been configured on the measuring unit configuration screen shown in FIG. 8, is stored in the transport control information memory 831 of the transport control device 8. The CPU 81 of the transport control device 8 obtains the information relating to the transport priority of the sample to be re-examined by referencing the selection information of the measuring units stored in the transport control information memory 831.

Whether or not re-examination is required may also be determined based on whether or not the obtained measurement data are within a normal range by storing a normal range of normal measurement values in the memory 93 of the control device 9 to be used for determining whether the measurement value of each measurement item is normal. In this case, an item may be provided for receiving the configuration of a normal range for each measurement item in the example of FIG. 8. Note that overlooking a sample that requires re-examination can be prevented before the occurrence and needless re-examination can be avoided by suitably configuring a normal range for each measurement item. A configured normal range for each measurement item is stored in the memory 93 of the control device 9 through the LAN 7.

Figure 9:
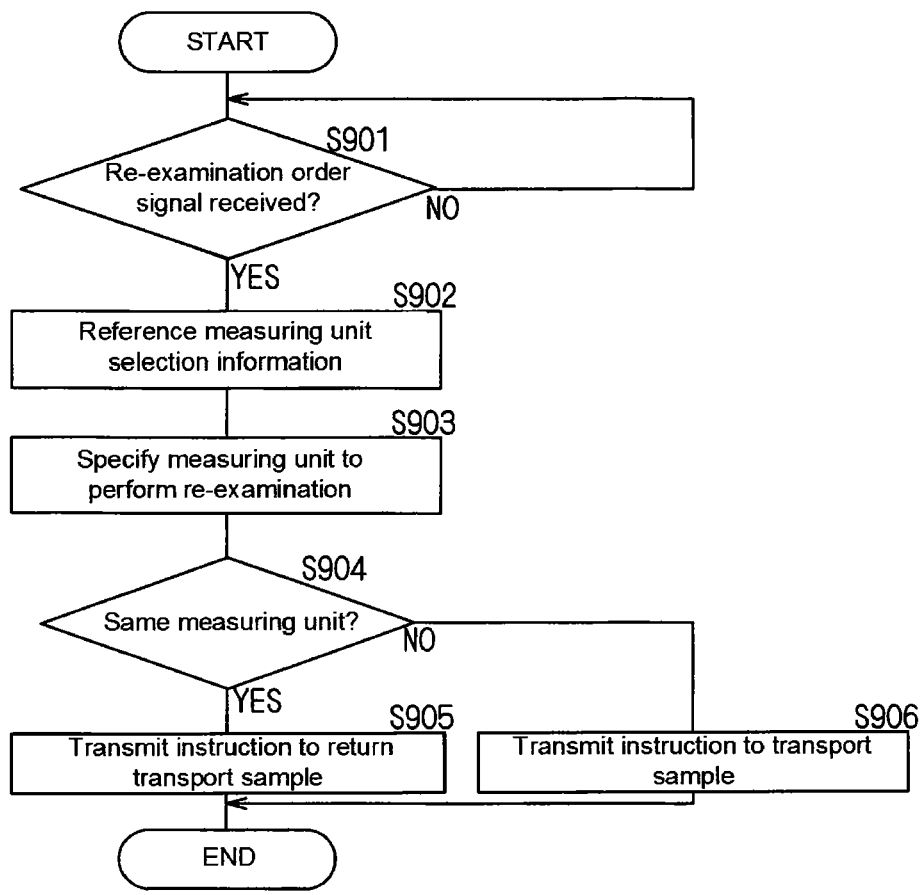
FIG. 9 is a flow chart showing the sequence of the re-examination process performed by the CPU of the transporting device of the first embodiment of the analyzer of the present invention.

FIG. 9 is a flow chart showing the sequence of the re-examination process performed by the CPU 81 of the transport control device 8 of the analyzer 1 of the first embodiment of the present invention. In FIG. 9, the CPU 81 of the transport control device 8 of the analyzer 1 of the first embodiment determines whether a re-examination order signal, which specifies the execution of re-examination, has been received from the CPU 91 of the control device 9. That is, the CPU 81 determines that re-examination is required when a re-examination order signal, which specifies the execution of re-examination, has been received from the CPU 91, and determines that re-examination is not required when a re-examination order signal, which specifies the execution of re-examination, has not been received from the CPU 91 within a predetermined time. Note that the CPU 91 of the control device 9 determines whether re-examination is required based on a predetermined condition, and transmits a re-examination order signal to the transport control device 8 when re-examination is required, and does not transmit a re-examination order signal when re-examination is not required. The CPU 81 then awaits reception when the CPU 81 has determined that a re-examination order signal has not been received (step S901: NO).

The re-examination order signal includes not only the information contained in the first order information, for example, the patient ID that identifies the patient and the sample ID contained in the barcode information as information identifying the sample, but also includes the measuring unit ID that identifies the measuring unit that performed the first examination, as well as the measurement items determined to require re-examination. When the CPU 81 has determined that a re-examination order signal has been received (step S901: YES), the CPU 81 references the measuring unit selection information stored in the transport control information memory 831 (step S902), and specifies the measuring unit that has the transport priority for the sample determined to require re-examination (step S903).

The CPU 81 determines whether the specified measuring unit is the same measuring unit that performed the first examination. When the CPU 81 determines that the specified measuring unit is the same measuring unit that performed the first examination (step S904: YES), the CPU 81 transmits instructions to transport the sample rack L holding the sample container T containing the sample to be re-examined back to the sample supplying position 35c of the measuring unit that performed the first examination (step S905).

When the CPU 81 determines that the specified measuring unit is not the same measuring unit that performed the first examination (step S904: NO), the CPU 81 transmits instructions to transport the sample rack L holding the sample container T containing the sample to be re-examined to the specified measuring unit (step S906).

According to the first embodiment described above, an analyzer is provided that is capable of realizing both a demand to perform re-examination by a different measuring unit than that which performed the first examination and a demand to obtain analysis results quickly for a sample determined to require re-examination by respectively receiving a configuration of the measuring unit that performed the first examination capable of obtaining an analysis result most quickly, or a configuration of another measuring unit different than the measuring unit that performed the first examination.

Second Embodiment

Since the structure of the analyzer 1 of the second embodiment of the present invention is identical to the structure of the analyzer 1 of the first embodiment and like parts are designated by like reference numbers, detailed description is therefore abbreviated. The second embodiment differs from the first embodiment in that the CPU 81 controls the sample transporting devices 3 so as to transport the sample to the measuring device capable of obtaining the analysis result in the shortest time by calculating, the analysis result obtaining time for each measuring unit, that is, the time needed to obtain the analysis result of re-examination at the moment the sample has been determined to require re-examination.

Accordingly, whether re-examination is performed by the measuring unit 5*a* that performed the first examination, or re-examination is performed by the measuring unit 5*b* or 5*c* does not need to be preconfigured by the user through the image display 120 of the transport control device 8, nor by the measuring unit configuration screen for configuring the measuring unit for performing the re-examination. That is, the processing is identical to when the "unassigned" configuration is specified in the first embodiment.

When a predetermined sample has been determined to require re-examination, the CPU 81 of the transport control device 8 detects the current position of the sample rack L holding the sample container T containing the sample to be re-examined, and calculates, for the measuring unit of each transport priority, the analysis result obtaining time from the aspiration of the transported sample until the analysis result is obtained. The analysis result obtaining time may also be the transport time from the current position of the sample rack L holding the sample container T containing the sample to be re-examined, or a time converted the number of sample awaiting measurement for each measuring unit. These times may also be combined, and index calculated for a comprehensive determination.

Figure 10:
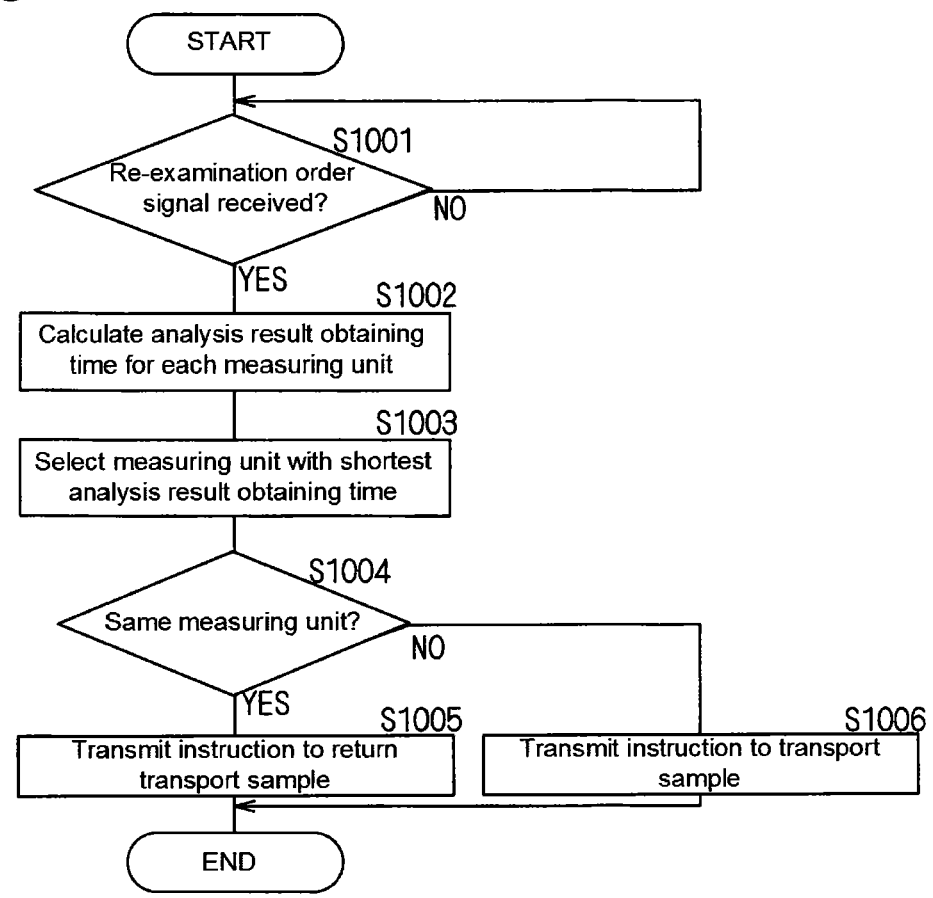
FIG. 10 is a flow chart showing the sequence of the re-examination process performed by the CPU of the transporting device of a second embodiment of the analyzer of the present invention.

FIG. 10 is a flow chart showing the sequence of the re-examination process performed by the CPU 81 of the transport control device 8 of the analyzer 1 of the second embodiment of the present invention. In FIG. 10, the CPU 81 of the transport control device 8 of the analyzer 1 of the second embodiment determines whether a re-examination order signal, which specifies the execution of re-examination, has been received from the CPU 91 of the control device 9 (step S1001). The CPU 81 then awaits reception when the CPU 81 has determined that a re-examination order signal has not been received (step S1001: NO).

The re-examination order signal includes not only the information contained in the first order information, for example, the patient ID that identifies the patient and the sample ID contained in the barcode information as information identifying the sample, but also includes the measuring unit ID that identifies the measuring unit that performed the first examination, as well as the measurement items determined to require re-examination. When the CPU 81 determines that a re-examination order signal has been received (step S1001: YES), the CPU 81 calculates the analysis result obtaining time for each measuring unit (step S1002). The CPU 81 selects the measuring unit with the shortest calculated analysis result obtaining time as the measuring unit for performing re-examination (step S1003).

The CPU 81 determines whether the selected measuring unit is the same measuring unit that performed the first examination (step S1004). When the CPU 81 determines that the selected measuring unit is the same measuring unit that performed the first examination (step S1004: YES), the CPU 81 transmits instructions to transport the sample rack L holding the sample container T containing the sample to be re-examined back to the sample supplying position 35*c* of the measuring unit that performed the first examination (step S1005).

When the CPU 81 has determined that the selected measuring unit is another measuring unit that is different than the measuring unit that performed the first examination (step S1004: NO), the CPU 81 transmits instruction to transport, to the selected measuring unit, the sample rack L holding the sample container T containing the sample to be re-examined (step S1006).

According to the second embodiment, the analysis result obtaining time required to re-examine a sample determined to require re-examination is calculated for each measuring unit, and the measuring unit with the shortest calculated analysis result obtaining time is selected as the measuring unit for re-examining the sample. The re-examination analysis result can be obtained early by automatically selecting the measuring unit with the shortest analysis result obtaining time as the measuring unit for performing the re-examination by performing controls to transport the sample determined to require re-examination to the selected measuring unit.

Note that not only is the measuring unit with the shortest calculated analysis result obtaining time selected as the measuring unit to perform the re-examination, the calculated analysis result obtaining times may also be displayed on the screen display 120 so that the user may also select a measuring unit to perform the re-examination based on the displayed analysis result obtaining times. In this case, the measuring unit with the shortest analysis result obtaining time can be selected as the measuring unit to perform re-examination by having the transport control device 8 perform controls to transport the sample determined to require re-examination to the selected measuring unit.

Third Embodiment

Figure 11:
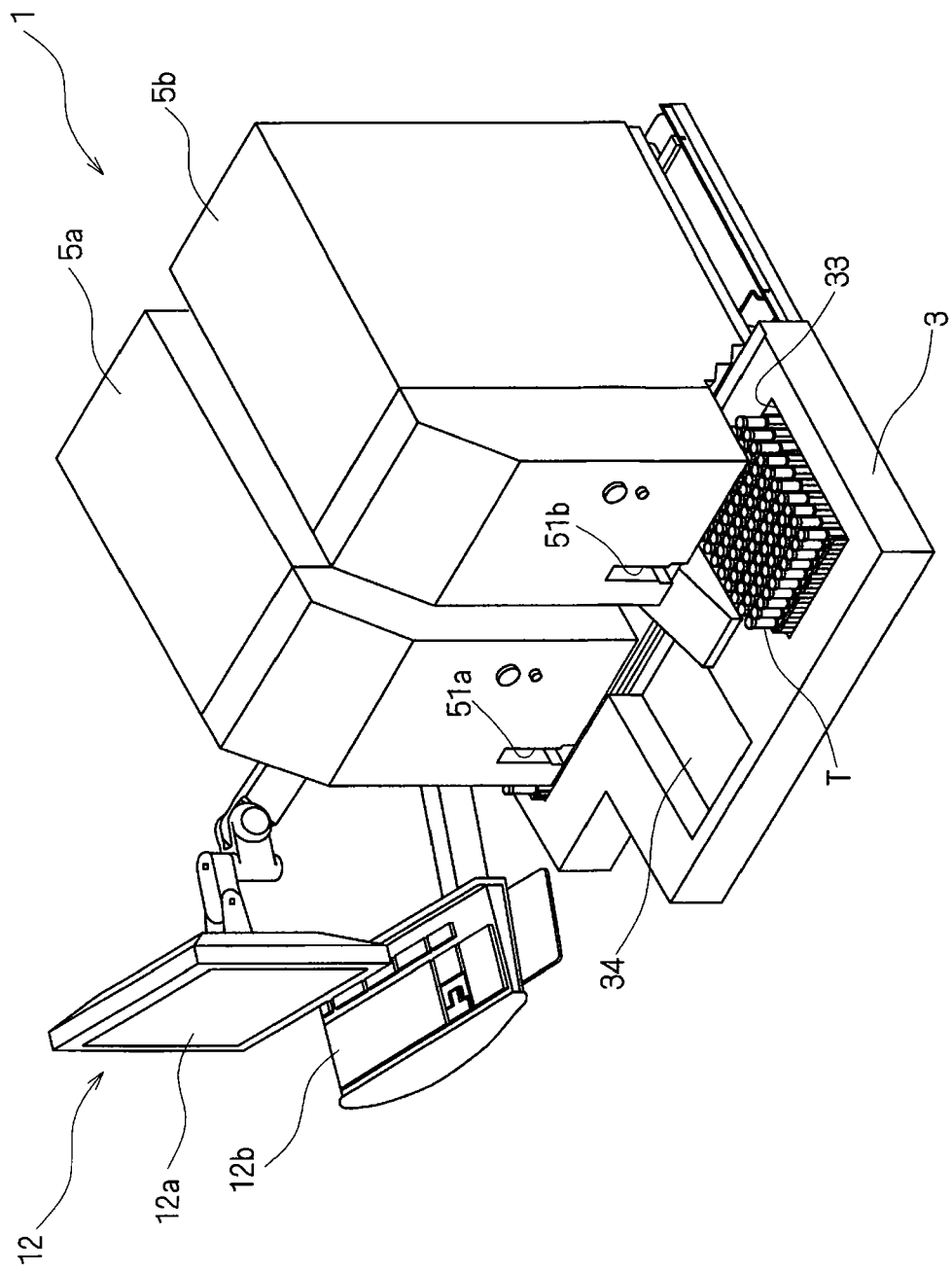
FIG. 11 is a schematic view briefly showing the structure of a third embodiment of the analyzer of the present invention.

FIG. 11 is a schematic view briefly showing the structure of the analyzer 1 of a third embodiment of the present invention. The analyzer 1 of the third embodiment of the present invention is provided with two measuring units including a first measuring unit 5*a* and second measuring unit 5*b* that are mutually of the same type, sample transporting device (transporting device) 3 disposed on the front side of the first measuring unit 5*a* and the second measuring unit 5*b*, and a control device 12 configured by a PC (personal computer) electrically connected to the first measuring unit 5*a*, second measuring unit 5*b*, and sample transporting device 3.

In the third embodiment, the first measuring unit 5*a* and the second measuring unit 5*b* are the same type of measuring unit, which measure a sample by measuring the same items using the same measurement principle. Note that in this case the same type of measuring unit not only includes the two measuring units 5*a* and 5*b* which measure a sample for completely identical measurement items, but also includes cases wherein a plurality of measurement items measured by the first measuring unit 5a and a plurality of measurement items measured by the measuring unit 5b are partially in common to both measuring units.

The first measuring unit 5a and the second measuring unit 5b are arranged in parallel. Furthermore, the first measuring unit 5a and the second measuring unit 5b measure predetermined measurement items of a sample aspirated, by an internal sample aspirating section and accessed through ports 51a and 51b provided in the housing, from sample container T held in a sample rack L transported by the sample transporting device 3.

Figure 12:
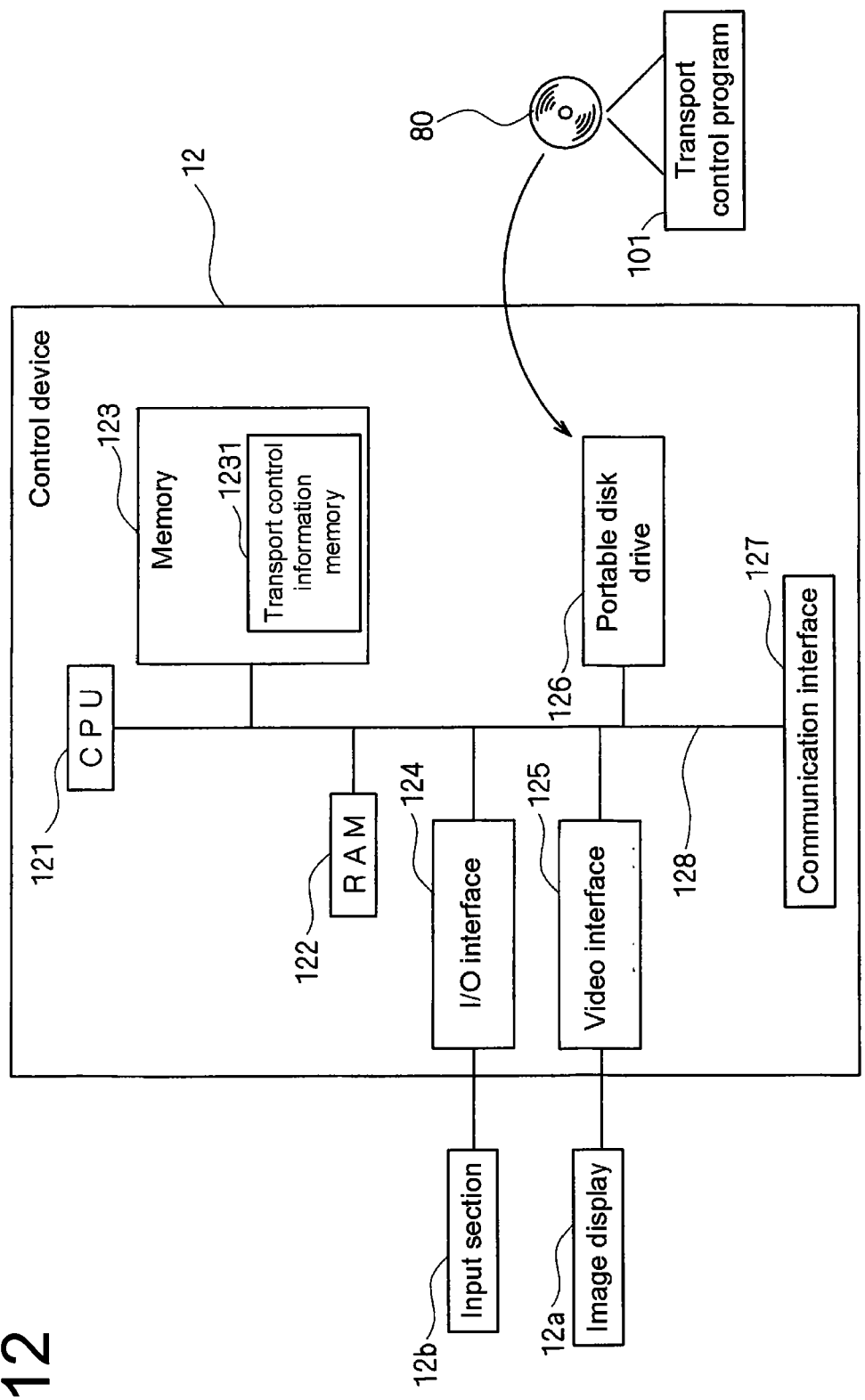
FIG. 12 is a block diagram showing the structure of the controller of the third embodiment of the analyzer of the present invention.

The control device 12 is configured by a personal computer (PC) or the like. FIG. 12 is a block diagram showing the structure of the control device 12 of the analyzer 1 of the third embodiment of the present invention. As shown in FIG. 12, the control device 12 is configured by a CPU 121, RAM 122, memory 123, I/O interface 124, video interface 125, portable disk drive 126, communication interface 127, and an internal bus 128, which is connected to all these hardware components.

The CPU 121 is connected to each hardware component of the control device 12 via the internal bus 128, so as to control the operation of each hardware component, and execute the functions of various software in accordance with a transport control program 101 stored in the memory 123. The RAM 122 is a volatile memory such as SRAM, DRAM or the like, and is used to expand loaded modules during the execution of the transport control program 101, and to store the temporary data generated during the execution of the transport control program 101.

The memory 123 is configured by an internal fixed storage device (hard disk), ROM or the like. The transport control program 101 stored in the memory 123 may be downloaded by the portable disk drive 126 from a portable recording medium 80 such as a DVD or CD-ROM on which information such as programs and data are recorded, and expanded from the memory 123 to the RAM 122 during execution of the program. Note that computer programs such as the transport control program 101 may also be downloaded from a peripheral computer connected to an external network through the communication interface 127. The memory 123 is provided with a transport control information memory 1231 for storing transport control information, such as the configuration item information for transport control, for each measuring unit 5a and 5b.

The communication interface 127 is connected to the internal bus 128 so that the control device 12 is capable of sending and receiving data to/from an external computer by means of connection to an external network such as a LAN, WAN, or the Internet.

The I/O interface 124 is connected to an input unit 12b such as a keyboard and mouse or the like, so as to receive data input. The video interface 125 is connected to an image display 12a such as a CRT monitor, LCD or the like to display predetermined images.

The brief structure of the sample transporting device 3 is identical to that of the first embodiment and like parts are designated by like reference numbers; therefore detailed description is abbreviated. Note that the reanalysis rack holder 33 is quadrilateral in shape in planar view, with a width slightly larger than the width of the sample rack L. The reanalysis rack holder 33 becomes lower in stages from the circumferential surface so that the sample rack L, which holds the reanalysis sample containers T, is mounted on the top surface.

The post-analysis rack holder 34 is also quadrilateral in shape in the planar view, with a width slightly larger than the width of the sample rack L. The post-analysis rack holder 34 becomes lower in stages from the circumferential surface so that the post analysis sample rack L is mounted on the top surface.

In the analyzer of the third embodiment of the present invention, the measuring unit 5a performs the first examination of the sample, and a determination is made as to whether a re-examination must be performed. When it has been determined that re-examination is required, the sample to be re-examined must be transported to the measuring unit which is to perform the re-examination. That is, when the re-examination is to be performed by the measuring unit that performed the first examination, the sample rack L holding the sample container T containing the sample to be re-examined must be transported back to the sample supplying position 35c. When the re-examination is performed by the measuring unit 5b, the sample rack L holding the sample container T containing the same to be re-examined must be transported to the adjacent measuring unit 5b.

Whether the measuring unit 5a performs the re-examination or the measuring unit 5b performs the re-examination can be preconfigured by the user through the image screen 12a of the control device 12. The measuring unit configuration screen displayed on the image display 12a is identical to that of first embodiment shown in FIG. 7.

When a "perform re-examination" configuration has been received, the configuration of the measuring unit (re-examination unit) to perform the re-examination (re-examination measuring unit) is received. When a "same unit" configuration has been received, the sample determined to require re-examination is re-examined by the measuring unit 5a that performed the first examination. Therefore, instructions are transmitted from the CPU 121 of the control device 12 to transport the sample rack L holding the sample container T containing the sample to be re-examined back to the sample supplying position 35c of the measuring unit 5a.

When a "different unit" configuration has been received, the sample determined to require re-examination is re-examined by the measuring unit 5b. The CPU 121 of the control device 12 issues instructions to transport the sample rack L holding the sample container T containing the sample to be re-examined to the sample supplying position 35c of the measuring unit 5b.

When an "assign" configuration has been received, the sample determined to require re-examination is re-examined by the measuring unit assigned by the user. Assigning a measuring unit may also be accomplished by, for example, a pulldown menu. In this case, instructions are transmitted from the CPU 121 of the control device 12 to transport the sample rack L holding the sample container T containing the sample to be re-examined to the sample supplying position 35c of the assigned measuring unit.

When an "unassigned" configuration has been received, the sample determined to require re-examination is re-examined by the measuring unit selected based on a predetermined condition. Note that the selection of any measuring unit may be accomplished by presetting predetermined selection conditions. For example, the measuring unit nearest the detected position of the sample rack L holding the sample container T containing the sample to be re-examined may be selected, or the measuring unit with the fewest number of sample racks L awaiting examination may be selected by precounting the number of sample racks L being transported to the respective measuring units 5a and 5b. The measuring unit that has the lightest processing load may also be selected by precalculating the processing loads of the processors 507 of the respective measuring units 5b and 5b. Instructions are then transmitted from the CPU 121 of the control device 12 to transport the sample rack L holding the sample container T containing the sample to be re-examined to the sample supplying position 35c of the selected measuring unit.

The selection information of the measuring unit for performing the re-examination, which has been configured on the measuring unit configuration screen shown in FIG. 7, is stored in the transport control information memory 1231 of the control device 12. The CPU 121 of the control device 12 obtains the information relating to the transport priority of the sample to be re-examined by referencing the selection information of the measuring units stored in the transport control information memory 1231.

The configuration of the measuring unit for performing the re-examination may also be received for each measurement item. In this case, a plurality of measurement items are prestored as determination conditions in the memory 123 of the control device 12, and the configuration of the selection conditions of the measuring unit are received when re-examination is to be performed for individual measurement items. Since the configuration screen of each measurement item of the measuring unit for performing the re-examination is identical to that of the first embodiment shown in FIG. 8, including the configuration content, detailed description is abbreviated.

The selection information of the measuring unit for performing the re-examination, which has been configured on the measuring unit configuration screen shown in FIG. 8, is stored in the transport control information memory 1231 of the control device 12. The CPU 121 of the control device 12 obtains the information relating to the transport priority of the sample to be re-examined by referencing the selection information of the measuring units stored in the transport control information memory 1231.

Note that, whether or not re-examination is required may also be determined based on whether or not the obtained measurement data are within a normal range by storing a normal range of normal measurement values in the memory 123 of the control device 12 to be used for determining whether the measurement value of each measurement item is normal. In this case, an item may be provided for receiving the configuration of a normal range for each measurement item in the example of FIG. 8. Note that overlooking a sample that requires re-examination can be prevented before the occurrence and needless re-examination can be avoided by suitably configuring a normal range for each measurement item. A normal range for each measurement item of the configuration can be stored in the memory 123 of the control device 12.

Figure 13:
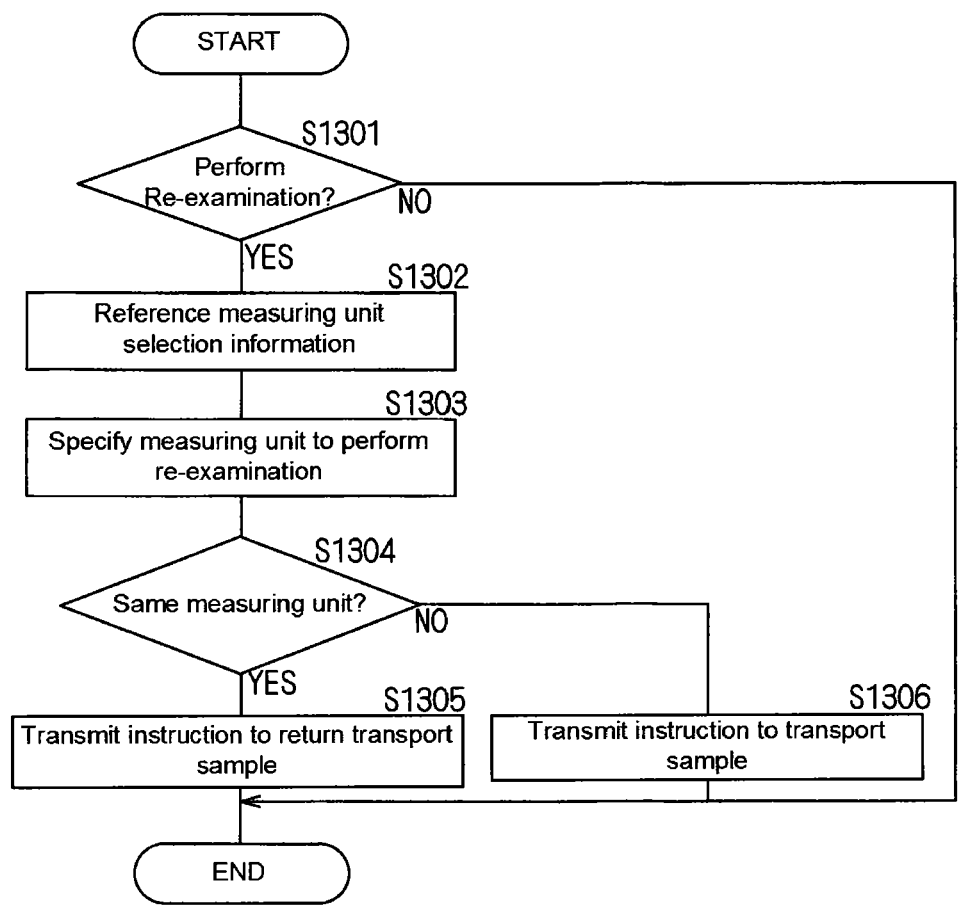
FIG. 13 is a flow chart showing the sequence of the re-examination process performed by the CPU of the transporting device of the third embodiment of the analyzer of the present invention.

FIG. 13 is a flow chart showing the sequence of the re-examination process performed by the CPU 121 of the control device 12 of the analyzer 1 of the third embodiment of the present invention. In FIG. 13, the CPU 121 of the control device 12 of the analyzer 1 of the third embodiment determines whether a sample for which an analysis result has been obtained will be re-examined (step S1301). When the CPU 121 determines not to re-examine (step S1301: NO), the CPU 121 end the process.

When the CPU 121 determines to perform re-examination (step S1301: YES), the CPU 121 references the measuring unit selection information stored in the transport control information memory 1231 (step S1302), and specifies the transport priority measuring unit to perform re-examination of the sample requiring re-examination (step S1303).

The CPU 121 determines whether the specified measuring unit is the same measuring unit that performed the first examination (step S1304). When the CPU 121 determines that the specified measuring unit is the same measuring unit that performed the first examination (step S1304: YES), the CPU 121 transmits instructions to transport the sample rack L holding the sample container T containing the sample to be re-examined back to the sample supplying position 35c of the measuring unit that performed the first examination (step S1305).

When the CPU 121 determines that the specified measuring unit is not the same measuring unit that performed the first examination (step S1304: NO), the CPU 121 transmits instructions to transport the sample rack L holding the sample container T containing the sample to be re-examined to the specified measuring unit (step S1306).

According to the third embodiment, the configuration of the measuring unit for performing re-examination of a sample can be optionally received. Therefore, it is possible to receive an explicit specification of the measuring unit that performed the first examination capable of obtaining an analysis result in the shortest time, or a different measuring unit than that which performed the first examination as the measuring unit for performing the re-examination. Accordingly, it is possible to perform the re-examination by the sample using the measuring unit that performed the first examination or using a different measuring unit when the analysis result of a predetermined measurement item is outside the normal range, and when a cause of the abnormality can not be specified.

Note that the present invention is not limited to the embodiments described above, and may be variously modified and rearranged insofar as such modification is within the scope of the invention. For example, the transport control device 8 and control device 9 may be singular or plural, or may be integratedly combined.

Furthermore, the re-examination order signal may be transmitted to the transport control device 8 when the control device 9 performs a determination as to whether a sample requires re-examination and has determined that the sample requires re-examination. However, the present invention is not limited to this configuration. For example, a host computer connected to the analyzer 1 through the LAN 7 may perform the determination as to whether a sample requires re-examination, and may transmit a re-examination order signal to the transport control device 8 when the host computer has determined that the sample requires re-examination.

What is claimed is:

1. An analyzing apparatus comprising:
   a transporting device for transporting a sample;
   a plurality of measuring units, each measuring unit measuring a sample transported by the transporting device, wherein the plurality of measuring units comprises three or more measuring units;
   a determination result obtainer for obtaining a determination result representing whether a sample requires remeasurement based on a measurement result by a predetermined measuring unit among the plurality of measuring units;
   a display unit configured to display a setting screen which is configured to selectively designate one measuring unit for remeasuring among the plurality of measuring units, wherein the display unit is further configured to receive a designation that any one of the other measuring units different from the predetermined measuring unit, which has initially measured the sample determined to be remeasured, remeasures the sample; and a transport controller for controlling the transporting device so as to transport the sample determined to be remeasured to the one measuring unit, wherein the transport controller:
  selects a measuring unit for remeasuring the sample from the other measuring units under predetermined condition, and controls the transport device so that the sample determined to be remeasured is transported to the selected measuring unit, when the display unit has received the designation that any one of the other measuring units different from the predetermined measuring unit remeasure the sample; and
  obtains respective processing loads of the plurality of measuring units, and selects the measuring unit with the lightest processing load as the measuring unit for remeasuring the sample.

2. The analyzing apparatus of claim 1, wherein
the display unit is further configured to receive the designation of the predetermined measuring unit, which has initially measured the sample determined to be remeasured, as the measuring unit for remeasuring the sample.

3. The analyzing apparatus of claim 1, wherein
the transport controller selects the measuring unit nearest to the sample as the measuring unit for remeasuring the sample from among the plurality of measuring units at the moment the determination result has been obtained by the determination result obtainer.

4. The analyzing apparatus of claim 1, wherein the transport controller obtains the number of samples transported to the respective measuring units, and selects the measuring unit with the fewest number of the samples as the measuring unit for remeasuring the sample.

5. The analyzing apparatus of claim 4, wherein
the memory stores a normal range of a measurement result for each predetermined measurement item as the determination condition.

6. The analyzing apparatus of claim 1, further comprising
a memory for storing a plurality of determination conditions for determining whether remeasurement of a sample is required, wherein
the display unit is further configured to receive a designation of one measuring unit for remeasuring the sample that has been determined to be remeasured for each determination condition.

7. The analyzing apparatus of claim 1, wherein
the transporting device comprises a transport line capable of transporting a sample in a flow direction and the reverse direction.

8. The analyzing apparatus of claim 1, further comprising
a time obtainer for obtaining a time required to re-measure the sample for each of the plurality of the measuring units; and
a display device for displaying the time required to re-measure the sample obtained by the time obtainer.

9. The analyzing apparatus of claim 1, wherein
each of the plurality of the measuring units is a blood cell counters for counting blood cells in a blood sample.

10. An analyzing apparatus comprising:
a transporting device for transporting a sample;
a plurality of measuring units, each measuring unit measuring a sample transported by the transporting device;
a determination result obtainer for obtaining a determination result representing whether the sample requires remeasurement based on the measurement result by a predetermined measuring unit among the plurality of measuring units;
a time obtainer for obtaining, for each of the plurality of the measuring units, a time required to re-measure the sample determined to be remeasured;
a selector for selecting, from among the plurality of measuring units, a measuring unit with the shortest time required to re-measure the sample as the measuring unit for remeasuring the sample; and
a transport controller for controlling the transporting device so as to transport the sample determined to be remeasured to the selected measuring unit, wherein
the time obtainer obtains the time required to re-measure the sample based on the current position of the sample determined to be remeasured, and
the time required to re-measure the sample is the time necessary for the transporting device to transport the sample from the current position to the measuring unit.

11. The analyzing apparatus of claim 10, wherein
the time required to re-measure the sample is the time necessary for the transporting device to transport the sample from the current position to the measuring unit and obtain a measurement result of the sample by the measuring unit.

12. The analyzing apparatus of claim 10, wherein
the time obtainer obtains the time required to re-measure the sample by obtaining the number of samples awaiting measurement by the respective measuring units.

13. The analyzing apparatus of claim 10, further comprising
a display device for displaying the time required to re-measure the sample obtained by the time obtainer.

14. The analyzing apparatus of claim 13, wherein
the display device displays the time required to re-measure the sample and a selection screen for selecting a measuring unit for remeasuring the sample; and
the selector is capable of receiving a selection of a measuring unit for remeasuring the sample through the selection screen.

15. An analyzing method executable by an analyzer comprising a transporting device for transporting a sample, and a plurality of measuring units, each measuring unit measuring a sample transported by the transporting device, the analyzing method comprising steps of:
  obtaining a determination result representing whether the sample requires remeasurement based on the measurement result by a predetermined measuring unit among the plurality of measuring units;
  obtaining, for each of the plurality of the measuring units, the time required to re-measure the sample determined to be remeasured based on the current position of the sample;
  selecting, from among the plurality of measuring units, the measuring unit with the shortest time required to re-measure the sample as the measuring unit for remeasuring the sample; and
  controlling the transporting device so as to transport the sample determined to be remeasured to the selected measuring unit,
  wherein the time required to re-measure the sample is the time necessary for the transporting device to transport the sample from the current position to the measuring unit.

16. An analyzing apparatus comprising:
a transporting device for transporting a sample;
a plurality of measuring units, each measuring unit measuring a sample transported by the transporting device, wherein the plurality of measuring units comprises three or more measuring units;

a determination result obtainer for obtaining a determination result representing whether a sample requires remeasurement based on a measurement result by a predetermined measuring unit among the plurality of measuring units;

a display unit configured to display a setting screen which is configured to selectively designate one measuring unit for remeasuring among the plurality of measuring units, wherein the display unit is further configured to receive a designation that any one of the other measuring units different from the predetermined measuring unit, which has initially measured the sample determined to be remeasured, remeasures the sample; and a transport controller for controlling the transporting device so as to transport the sample determined to be remeasured to the one measuring unit, wherein the transport controller:

selects a measuring unit for remeasuring the sample from the other measuring units under predetermined condition, and controls the transport device so that the sample determined to be remeasured is transported to the selected measuring unit, when the display unit has received the designation that any one of the other measuring units different from the predetermined measuring unit remeasure the sample; and obtains the number of samples transported to the respective measuring units, and selects the measuring unit with the fewest number of the samples as the measuring unit for remeasuring the sample.

17. The analyzing apparatus of claim 16, further comprising a memory for storing a plurality of determination conditions for determining whether remeasurement of a sample is required, wherein the display unit is further configured to receive a designation of one measuring unit for remeasuring the sample that has been determined to be remeasured for each determination condition.

18. The analyzing apparatus of claim 17, wherein the memory stores a normal range of a measurement result for each predetermined measurement item as the determination condition.

19. The analyzing apparatus of claim 16, wherein the transporting device comprises a transport line capable of transporting a sample in a flow direction and the reverse direction.

20. The analyzing apparatus of claim 16, further comprising a time obtainer for obtaining a time required to re-measure the sample for each of the plurality of the measuring units; and a display device for displaying the time required to re-measure the sample obtained by the time obtainer.

* * * * *